US00PP19407P2

(12) United States Plant Patent
Ruys

(10) Patent No.: US PP19,407 P2
(45) Date of Patent: Nov. 4, 2008

(54) ***MANDEVILLA* PLANT NAMED 'SUNPARAVEL'**

(50) Latin Name: *Mandevilla hybrida*
Varietal Denomination: Sunparavel

(75) Inventor: Theo Ruys, Leimuiderbrug (NL)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/012,483

(22) Filed: Jan. 31, 2008

(51) Int. Cl.
*A01H 5/00* (2006.01)

(52) U.S. Cl. ..... Plt./232

(58) Field of Classification Search ..... Plt./232
See application file for complete search history.

(56) References Cited

PUBLICATIONS

PBR 20061250—Sunparavel, European Plant Breeder's Right published Aug. 15, 2006.*

* cited by examiner

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Mandevilla* plant named 'Sunparavel', characterized by its upright and vining plant habit; relatively small glossy foliage; freely flowering habit; dark red purple-colored flowers; and long flowering period.

2 Drawing Sheets

Botanical designation: *Mandevilla hybrida.*
Cultivar denomination: 'Sunparavel'.

BACKGROUND OF THE INVENTION

The present invention relates to a new and distinct cultivar of *Mandevilla,* botanically known as *Mandevilla hybrida* and hereinafter referred to by the name 'Sunparavel'.

The new *Mandevilla* is a naturally-occurring branch mutation of the *Mandevilla hybrida* cultivar Sunmandecrim, disclosed in U.S. Plant Pat. No. 15,539. The new *Mandevilla* was discovered and selected by the Inventor from within a population of plants of the cultivar Sunmandecrim in a controlled environment in Amstelveen, The Netherlands in April, 2005.

Asexual reproduction of the new cultivar by cuttings in Leimuiderbrug, The Netherlands, since June, 2005, has shown that the unique features of this new *Mandevilla* are stable and reproduced true to type in successive generations.

SUMMARY OF THE INVENTION

Plants of the cultivar Sunparavel have not been observed under all possible environmental conditions. The phenotype may vary somewhat with variations in environment such as temperature and light intensity without, however, any variance in genotype.

The following traits have been repeatedly observed and are determined to be the unique characteristics of 'Sunparavel'. These characteristics in combination distinguish 'Sunparavel' as a new and distinct cultivar:

1. Upright and vining plant habit.
2. Relatively small glossy foliage.
3. Freely flowering habit.
4. Dark red purple-colored flowers.
5. Long flowering period.

Plants of the new *Mandevilla* differ primarily from plants of the parent, the cultivar Sunmandecrim, in flower color as plants of the cultivar Sunmandecrim have red-colored flowers. In addition, plants of the new *Mandevilla* have shorter lateral branches than plants of the cultivar Sunmandecrim.

Plants of the new *Mandevilla* can be compared to plants of the *Mandevilla* cultivar Sunparabeni, disclosed in a U.S. Plant Patent application filed concurrently, and the *Mandevilla* cultivar Sunparapibra, disclosed in a U.S. Plant Patent application filed concurrently. Plants of the new *Mandevilla* differ primarily from plants of the cultivars Sunparabeni and Sunparapibra in flower color.

Plants of the new *Mandevilla* can also be compared to plants of the *Mandevilla* cultivar Sunmandecos, disclosed in U.S. Plant Pat. No. 15,202. In side-by-side comparisons conducted in Higashiomi, Shiga, Japan, plants of the new *Mandevilla* differed from plants of the cultivar Sunmandecos in the following characteristics:

1. Plants of the new *Mandevilla* had shorter leaves than plants of the cultivar Sunmandecos.
2. Plants of the new *Mandevilla* were more freely flowering than plants of the cultivar Sunmandecos.
3. Plants of the new *Mandevilla* and the cultivar Sunmandecos differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Mandevilla.*

The photograph on the first sheet comprises a side perspective view of a typical flowering plant of 'Sunparavel' grown in a container.

The photograph on the second sheet is a close-up view of a typical flower of 'Sunparavel'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the summer in an outdoor nursery in Higashiomi, Shiga, Japan for about four months. During the production of the plants, day temperatures averaged 25° C. and night temperatures averaged 15° C.

Botanical classification: *Mandevilla hybrida* cultivar Sunparavel.

Parentage: Naturally-occurring branch mutation of the *Mandevilla hybrida* cultivar Sunmandecrim, disclosed in U.S. Plant Pat. No. 15,539.

Propagation:

*Type.*—By vegetative cuttings.

*Time to initiate roots.*—About two weeks at 23° C. to 25° C.

*Time to produce a rooted young plant.*—About 40 days at 23° C. to 25° C.

*Root description.*—Fibrous, fleshy; light brown in color.

*Rooting habit.*—Freely branching.

Plant description:

*Form.*—Perennial. Upright and vining plant habit. Vigorous growth habit.

*Plant height.*—About 140 cm.

*Lateral branch description.*—Length: About 140 cm. Diameter: About 2 mm. Internode length: About 2 cm to 15 cm. Strength: Strong. Texture: Smooth, glabrous. Color: Young: 146A overlain with close to N170B. Mature: N199A.

Foliage description:

*Arrangement.*—Opposite, simple.

*Length.*—About 5.5 cm.

*Width.*—About 4.4 cm.

*Shape.*—Elliptic.

*Apex.*—Cuspidate.

*Base.*—Rounded to cordate.

*Margin.*—Entire.

*Texture, upper and lower surfaces.*—Smooth, glabrous.

*Luster, upper and lower surfaces.*—Glossy.

*Venation pattern.*—Pinnate, reticulate.

*Color.*—Developing foliage, upper surface: 146A. Developing foliage, lower surface: 146C. Fully expanded foliage, upper surface: 137A; venation, 145B. Fully expanded foliage, lower surface: 146B; venation, 145B.

*Petiole length.*—About 1.4 cm.

*Petiole diameter.*—About 1.4 mm.

*Petiole texture, upper and lower surfaces.*—Smooth, glabrous.

*Petiole color, upper and lower surfaces.*—145B.

Flower description:

*Flower type and habit.*—Single salverform flowers; flowers racemose; flowers face mostly outwardly. Flowers not persistent. Freely flowering habit, about five flowers per inflorescence.

*Natural flowering season.*—Long flowering period; early summer to late autumn in Japan; flowering continuous during this period.

*Flower longevity on the plant.*—About seven to ten days. Flowers not persistent.

*Fragrance.*—Slightly fragrant; pleasant.

*Inflorescence height.*—About 11.3 cm.

*Inflorescence diameter.*—About 13 cm.

*Flowers.*—Appearance: Flared trumpet, corolla fused, five-parted; petals imbricate; flowers roughly star-shaped. Diameter: About 7.7 cm. Depth (length): About 6.3 cm. Throat diameter: About 1.7 cm. Tube length: About 5.3 cm. Tube diameter, base: About 4 mm.

*Flower buds.*—Length: About 7.4 cm. Diameter: About 1.4 cm. Shape: Lenticular. Color: 59B.

*Corolla.*—Arrangement/appearance: Single whorl of five petals, fused into flared trumpet; petals imbricate. Petal length: About 3.4 cm. Petal width: About 2.5 cm. Petal shape: Spatulate. Petal apex: Acuminate. Petal margin: Entire, slightly undulate. Petal texture, upper and lower surfaces: Smooth, glabrous. Color: Petal, when opening, upper surface: 59B. Petal, when opening, lower surface: 59B; longitudinal lines, N155B. Petal, fully opened, upper and lower surfaces: 59C; color becoming closer to 186A with development. Tube: 59B. Throat: N25B.

*Sepals.*—Arrangement/appearance: Five per flower in a single whorl; fused. Length: About 7.2 mm. Width: About 2 mm. Shape: Lanceolate. Apex: Acute. Margin: Entire. Texture, upper and lower surfaces: Smooth, glabrous. Color, immature, upper and lower surfaces: 144B; towards the apex, 181C. Color, mature, upper and lower surfaces: 182C; towards the apex, 181C.

*Peduncles.*—Length: About 5 cm. Diameter: About 2.3 mm. Texture: Smooth, glabrous. Strength: Flexible, but strong. Color: 145C.

*Pedicels.*—Length: About 2.2 cm. Diameter: About 2.1 mm. Texture: Smooth, glabrous. Strength: Flexible, but strong. Color: 146A.

*Reproductive organs.*—Stamens: Quantity/arrangement: Typically five; filaments fused to corolla; anthers, connivent. Anther shape: Elliptic. Anther size: About 1 cm by 1.5 mm. Anther color: Close to 18B. Pollen amount: Scarce. Pollen color: Close to 155B. Pistils: Quantity: Typically one. Pistil length: About 2 cm. Stigma shape: Conical. Stigma color: 145B. Style color: 145C. Ovary color: 144B.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 4° C. to about 30° C.

It is claimed:

1. A new and distinct *Mandevilla* plant named 'Sunparavel' as illustrated and described.

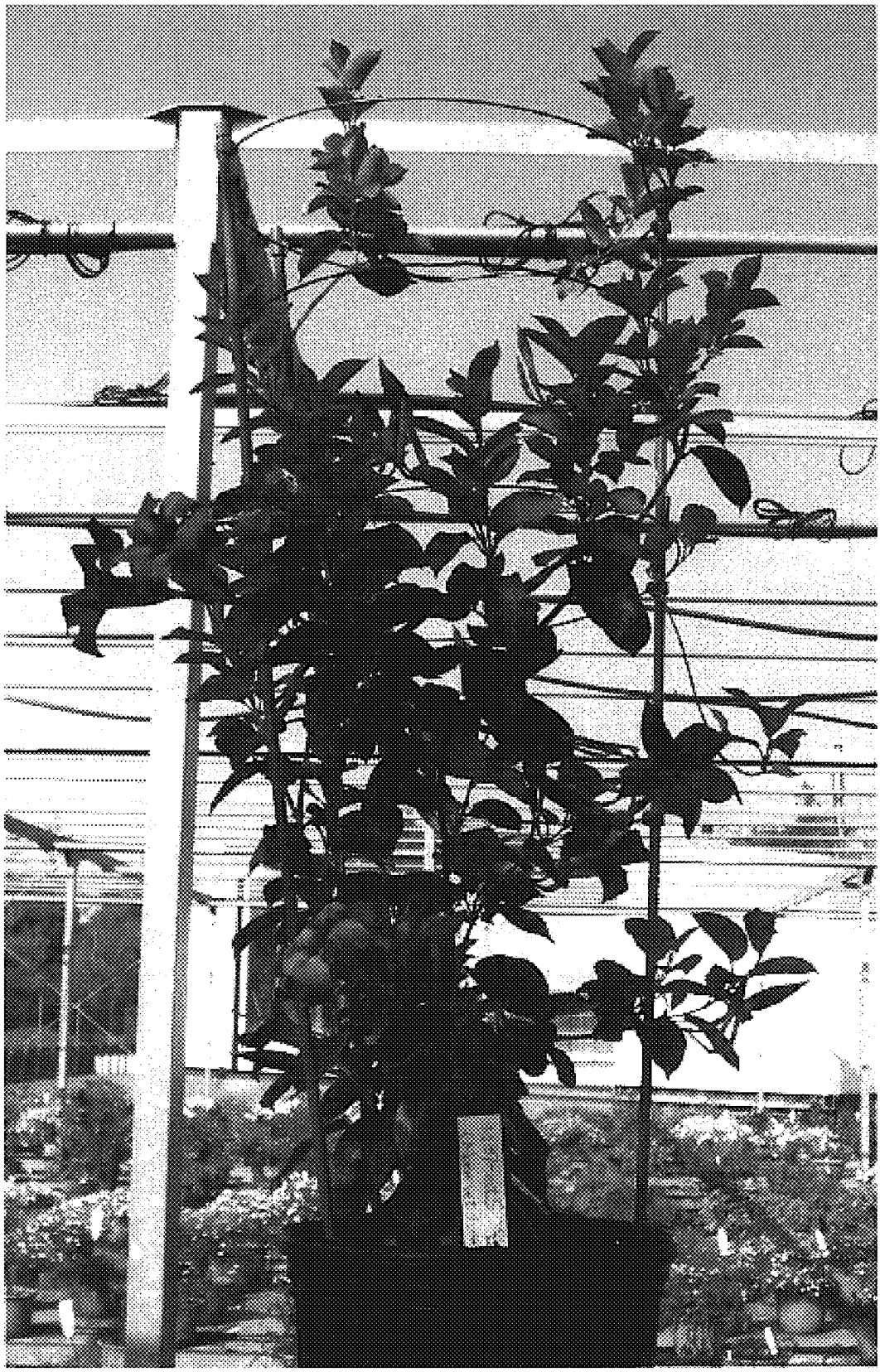

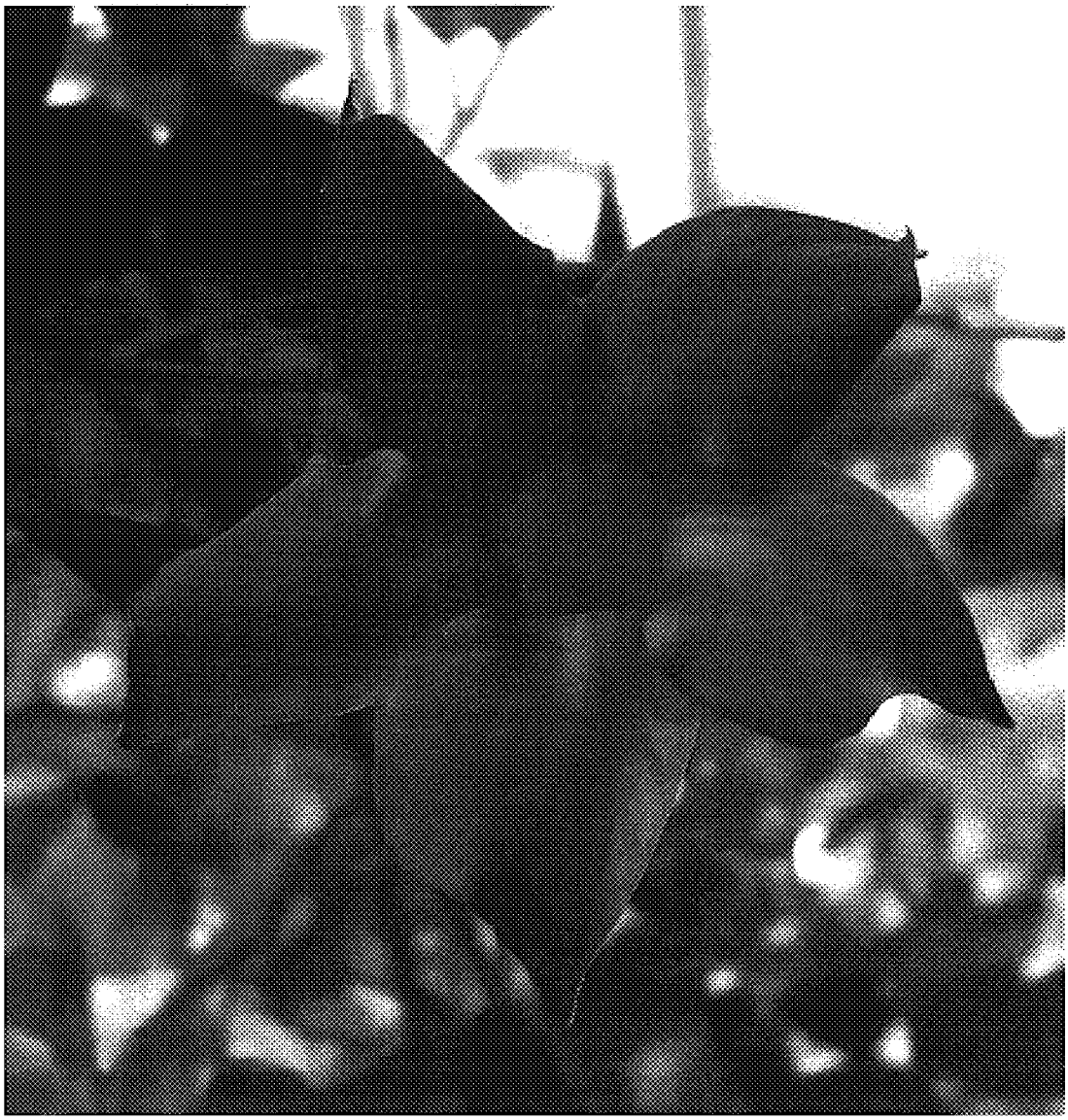

* * * * *